US011324464B2

(12) United States Patent
Thornton, III et al.

(10) Patent No.: US 11,324,464 B2
(45) Date of Patent: May 10, 2022

(54) STORAGE SLOTS FOR DIGITAL RADIOGRAPHIC DETECTORS

(71) Applicant: CARESTREAM HEALTH, INC., Rochester, NY (US)

(72) Inventors: Edward J. Thornton, III, Helena, AL (US); Todd R. Minnigh, Brookfield, WI (US)

(73) Assignee: Carestream Health, Inc., Rochester, NY (US)

( * ) Notice: Subject to any disclaimer, the term of this patent is extended or adjusted under 35 U.S.C. 154(b) by 156 days.

(21) Appl. No.: 16/935,243

(22) Filed: Jul. 22, 2020

(65) Prior Publication Data

US 2021/0022696 A1   Jan. 28, 2021

Related U.S. Application Data

(60) Provisional application No. 62/878,424, filed on Jul. 25, 2019.

(51) Int. Cl.
*A61B 6/00* (2006.01)

(52) U.S. Cl.
CPC ............. *A61B 6/4405* (2013.01); *A61B 6/54* (2013.01); *A61B 6/4216* (2013.01); *A61B 2560/0437* (2013.01)

(58) Field of Classification Search
CPC ......... A61B 6/56; A61B 6/4405; A61B 6/464; A61B 6/4283; A61B 6/4452; A61B 6/4291; A61B 6/4482; G03B 42/045
See application file for complete search history.

(56) References Cited

U.S. PATENT DOCUMENTS

2018/0059258 A1\*   3/2018   MacLaughlin ......... H02J 7/027

\* cited by examiner

*Primary Examiner* — Don K Wong

(57) ABSTRACT

A mobile radiography apparatus includes a moveable transport frame and an adjustable support arm attached thereto to support an x-ray source. At least one digital detector storage slot in the transport frame is configured to receive and to controllably lower at least one portable radiographic detector into the slot at a controlled speed.

20 Claims, 5 Drawing Sheets

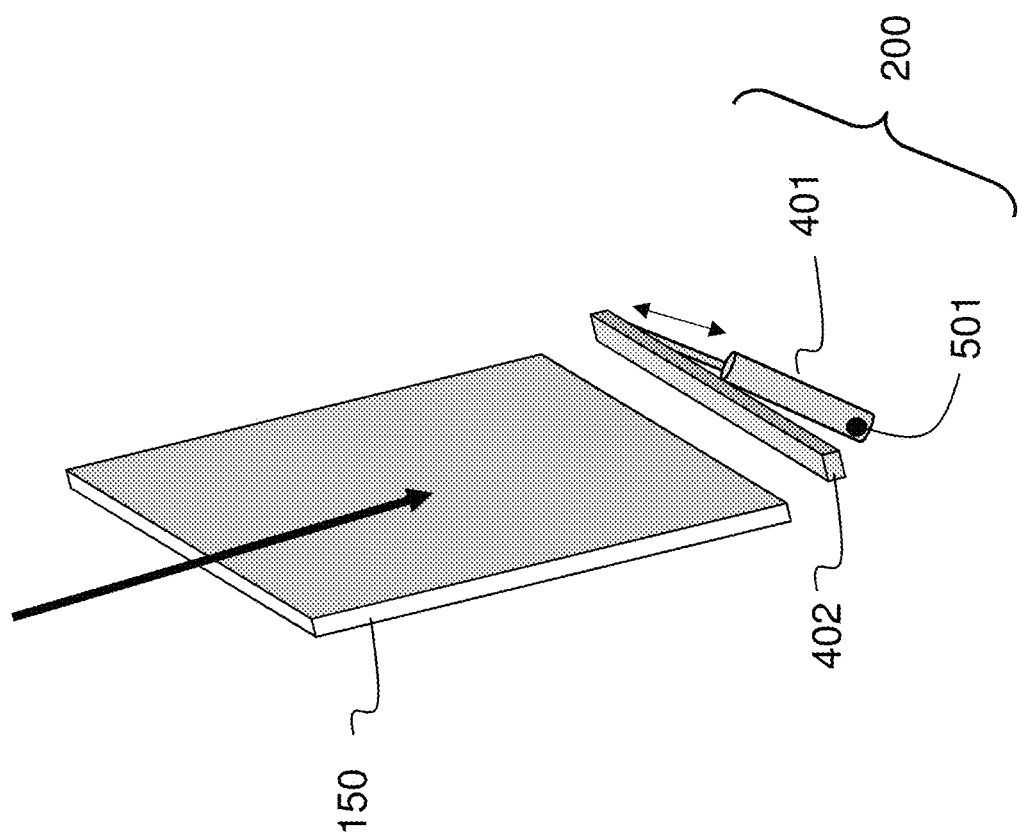

STORAGE SLOTS FOR DIGITAL RADIOGRAPHIC DETECTORS

CROSS REFERENCE TO RELATED APPLICATIONS

This application claims priority to U.S. Patent Application Ser. No. 62/878,424, filed Jul. 25, 2019, in the name of Thornton et al., and entitled STORAGE SLOTS FOR DIGITAL RADIOGRAPHIC DETECTORS, which is hereby incorporated by reference herein in its entirety.

FIELD OF THE INVENTION

The invention relates generally to the field of medical imaging, and in particular to storage of portable radiographic imaging apparatus. More specifically, the invention relates to a mobile radiography apparatus including slots for storing at least one portable digital radiographic detector.

BACKGROUND

Mobile carts are employed in medical facilities to move medical equipment between locations. One type of mobile cart includes an x-ray source used to capture digital x-ray images on an x-ray detector. Medical x-ray images can be captured using various digital or analog techniques.

Mobile x-ray apparatus are of particular value in intensive care unit (ICU) and other environments where timely acquisition of a radiographic image is important. Because portable carts can be wheeled around the ICU or other area and brought directly to the patient's bedside, a portable x-ray imaging apparatus allows an attending physician or clinician to have recent information on the condition of a patient and helps to reduce the risks entailed in moving patients to stationary equipment in the radiological facility. However, there is a need for improvements in mobile x-ray cart design to allow such apparatuses to safely store portable digital radiographic detectors. The discussion above is merely provided for general background information and is not intended to be used as an aid in determining the scope of the claimed subject matter.

SUMMARY

A mobile radiography apparatus includes a moveable transport frame and an adjustable support arm attached thereto to support an x-ray source. At least one digital detector storage slot in the transport frame is configured to receive and to lower at least one portable radiographic detector into the slot at a controlled rate.

In one embodiment, a mobile radiography apparatus includes a moveable transport frame, an adjustable support structure coupled to the moveable transport frame, an x-ray source coupled to the adjustable support structure, and at least one detector storage slot configured to receive and to controllably lower at least one portable radiographic detector into the storage slot at a controlled rate.

In one embodiment, a storage slot for a radiographic detector includes a receiving mechanism is configured to prevent the radiographic detector from free falling into the storage slot. A damping apparatus connected to the receiving mechanism controllably lowers the digital detector into the storage slot.

The summary descriptions above are not meant to describe individual separate embodiments whose elements are not interchangeable. In fact, many of the elements described as related to a particular embodiment can be used together with, and possibly interchanged with, elements of other described embodiments. Many changes and modifications may be made within the scope of the present invention without departing from the spirit thereof, and the invention includes all such modifications.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings below are intended to be drawn neither to any precise scale with respect to relative size, angular relationship, relative position, or timing relationship, nor to any combinational relationship with respect to interchangeability, substitution, or representation of a required implementation, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 5 is a diagram of an alternative configuration of a hydraulic or pneumatic damping assembly.

DESCRIPTION OF EXEMPLARY EMBODIMENTS

Figure 1:
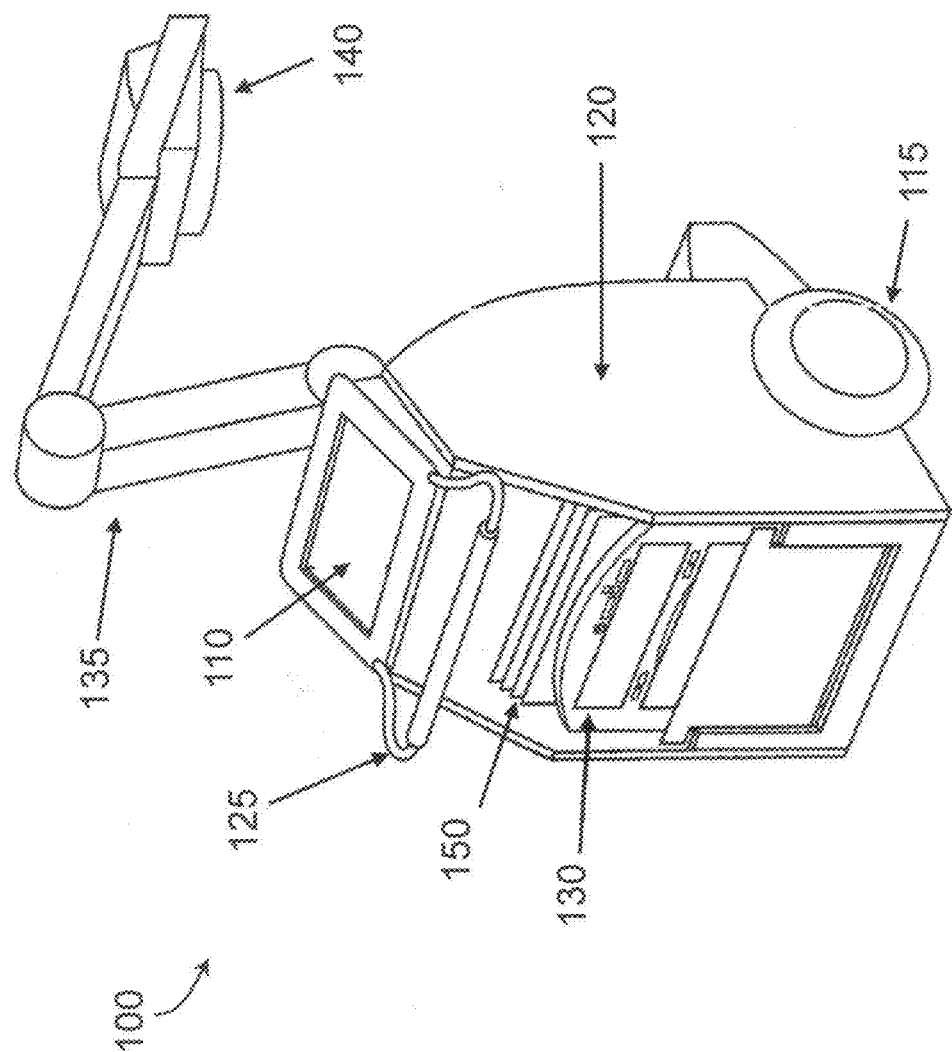
FIG. 1 is a diagram that shows a perspective view of a mobile radiography apparatus.

The following is a description of exemplary embodiments of the invention, reference being made to the drawings in which the same reference numerals identify the same elements of structure in each of the several figures. FIG. 1 shows a perspective view of a mobile radiography apparatus 100 that can include a storage area 130 for one or more portable radiographic detectors or flat panel detectors 150. The exemplary mobile x-ray, or radiographic, apparatus of FIG. 1 can be employed for computed radiography (CR)

and/or digital radiography (DR). As shown in FIG. 1, a mobile radiography apparatus 100 can include a moveable transport frame 120 that includes a display 110. For mobility, the mobile radiographic apparatus 100 can have one or more wheels 115 and one or more handle grips 125, typically provided at waist-level, arm-level, or hand-level, that help to guide the mobile radiographic apparatus 100 to its intended location. A self-contained battery pack (e.g., rechargeable) in the frame or elsewhere can provide source power, which can reduce or eliminate the need for operation near a power outlet. Further, the self-contained battery pack can provide for motorized transport.

Mounted to frame 120 is a support member, or support arm, 135 that supports a variably movable x-ray source 140, also called an x-ray tube, tube head, or generator that can be mounted to the support member 135. In one embodiment, the tube head or x-ray source 140 can be rotatably coupled to the support column 135. In the embodiment shown in FIG. 1, an articulated member of the support column that bends at a joint mechanism can allow movement of the x-ray source 140 over a range of vertical and horizontal positions. Height settings for the x-ray source 140 can range from low height for imaging feet and lower extremities to shoulder height and above for imaging the upper body portions of patients in various positions.

For storage, the mobile radiographic apparatus 100 can include a storage area/holder 130 for holding/storing one or more digital radiographic (DR) detectors 150 or computed radiography (stimulated phosphor) cassettes. The area/holder can be storage area 130 disposed on the frame 120 configured to removably retain at least one digital radiography (DR) detector 150. The storage area 130 can be configured to hold a plurality of detectors 150 and can also be configured to hold one size or multiple sizes of DR detectors 150 or cassettes.

Figures 2A, 2B:
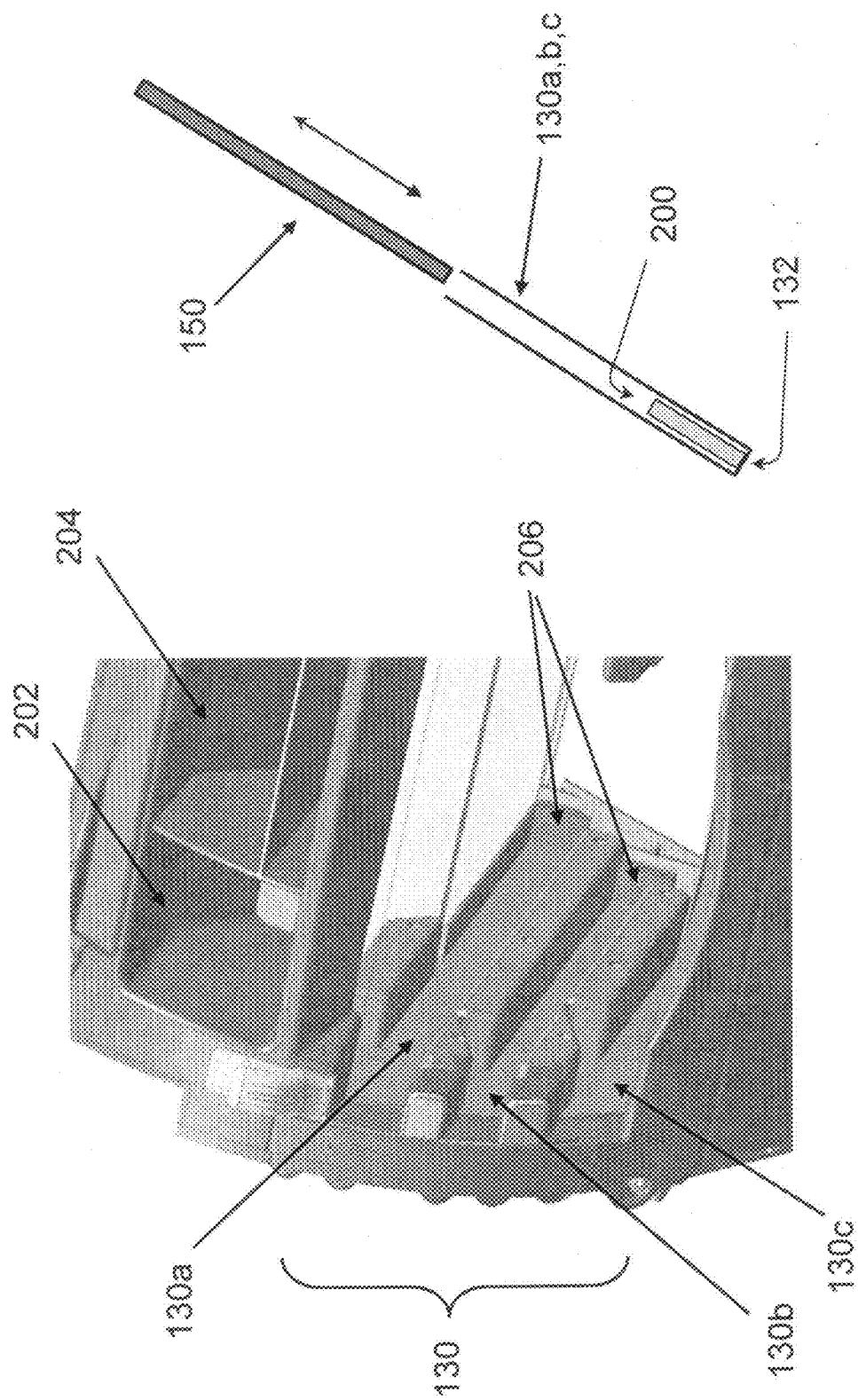
FIGS. 2A-2B are diagrams that illustrate a perspective view and a schematic view of a detector storage area in a mobile x-ray cart.

FIG. 2A is a close-up partial perspective view of the DR detector storage area 130. The storage area 130 can include a plurality of individual slots 130a, 130b, 130c, such as detector slot 130a for large DR detectors 150, 130b for smaller DR detectors 150, and 130c for even smaller DR detectors 150. Exemplary detectors 150 can include a detector with or without an attached grid and/or additional detector accessories such as but not limited to additional antenna, power supply or additional electronics. Additional storage areas for materials at the mobile radiography apparatus 100 can include storage 202 (e.g., for rubber gloves) and additional storage 204. As shown schematically in FIG. 2B, a DR detector 150 may be inserted and removed from a storage slot 130a, 130b or 130c manually. A damping assembly 200 may be positioned in the storage slots 130a, 130b, 130c, to prevent a DR detector 150 manually inserted therein from significantly impacting a bottom surface 132 of the storage slot due to force of gravity if the DR detector 150 is manually released during insertion such that the detector 150 falls to the bottom of the storage slot.

In one embodiment, the storage slot 130a, 130b, 130c, can include a suspension mechanism or cushioning mechanism positioned at the bottom of the slots 130a, 130b, 130c, including a pad 206 made from a soft, rubber foam, or soft elastomeric material to absorb an impact to the DR detector 150 when the detector is dropped into the storage slot 130a, 130b, 130c. In one embodiment, in order to prevent impacts caused when DR detectors 150 are dropped into bins or slots 130a, 130b, 130c, and strike the bottom 132 thereof, a damping assembly 200 may be included in the slot 130a, 130b, 130c, to controllably receive the DR detector 150 being dropped or inserted into the slot, using one of several different damping assemblies 200 described herein.

Figure 3:
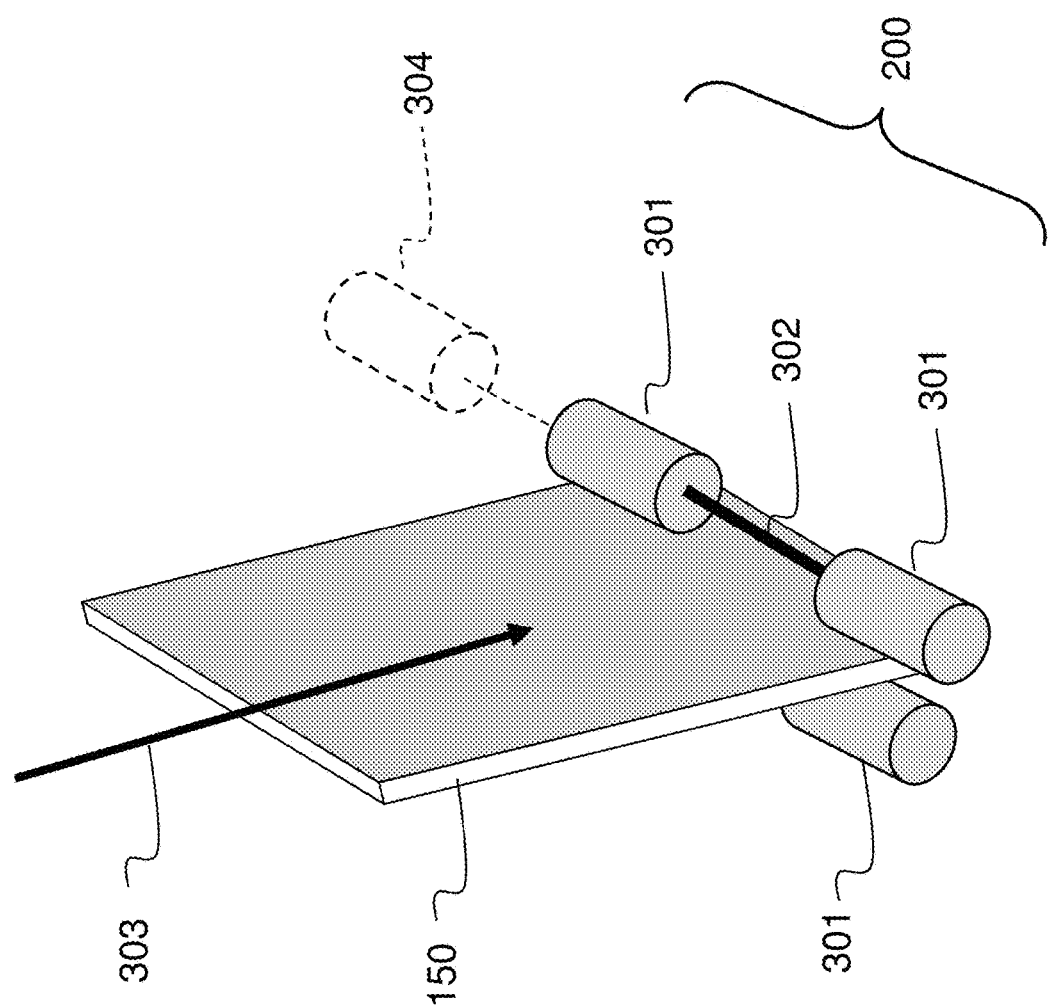
FIG. 3 is a schematic diagram of a damping assembly for use in a radiographic detector storage slot.

FIG. 3 illustrates a damping assembly 200 including pinch rollers 301 which are spaced apart slightly less than a thickness of a detector 150 being inserted into the slot 130. Thereby, the rollers 301 contact the detector 150 on opposite major surfaces thereof to frictionally engage the detector and prevent the detector from sliding past the rollers. The rollers 301 themselves may be rotationally damped to prevent free wheeling rotational motion of the rollers 301 caused by the weight of the detector 150. In one embodiment, there may be one roller 301 on each side of the detector 150 configured to frictionally engage the detector 150 or, as shown in FIG. 3, a plurality of rollers 301 on each side of the detector 150 are connected together by an axle 302 so that the rollers 301 roll together at the same rate. The damped rollers 301 are thereby allowed to rotate at a preselected slow rate to controllably lower the detector 301 into the slot by force of gravity in the direction indicated by arrow 303 when the detector 150 is manually inserted into the storage slot 130 and released by a user. The damped rollers 301 may be individually damped or they may be attached, such as by a shaft, to a damping mechanism 304 which allows the rollers 301 to rotate at a controlled rate, or speed, to thereby slowly lower the detector 150 as against the force of earth gravity. The damping mechanism 304, may include a set of gears having a selected ratio that limits rotational acceleration of the rollers 301, or the damping mechanism 304 may include a friction brake mechanism that prevents rotational acceleration using a friction brake pad. The rollers 301 may include a type of elastomeric or foam rubber material with a preselected firmness to contact the surfaces of the detector 150 to allow detectors of various thicknesses to be gripped, or frictionally engaged, by the rollers 301 when the detector 150 is inserted therebetween. The selected material should include properties that are pathogen resistant and easily disinfected. The roller's damped rotation slowly guides the detector 150 to a resting position in the slot 130a, 130b, 130c, at a very low impact force when the detector 150 contacts the bottom 132 of the slot 130a, 130b, 130c, or otherwise reaches its lowest resting position within the slot 130a, 130b, 130c. When a detector 150 is manually removed from its lowest resting position within a storage slot 130a, 130b, 130c, the damping mechanism 304 is returned to its initial rotational position by movement of the detector 150 upward and out of the slot 130a, 130b, 130c. In one embodiment, the damping mechanism 304 may be configured such that its rotational acceleration is attenuated in one direction, i.e. when a detector 150 is inserted into the slot 130a, 130b, 130c, and its rotational acceleration is free-wheeling in an opposite direction when the detector 150 is removed upward from the storage slot 130a, 130b, 130c, thereby not resisting, or slowing, manual removal of the detector 150 from the slot 130a, 130b, 130c. In this embodiment, the damping mechanism 304 is configured to be biased to rotate the rollers 301 to an initial position when the detector (weight) is removed from the slot 130a, 130b, 130c.

Figure 4:
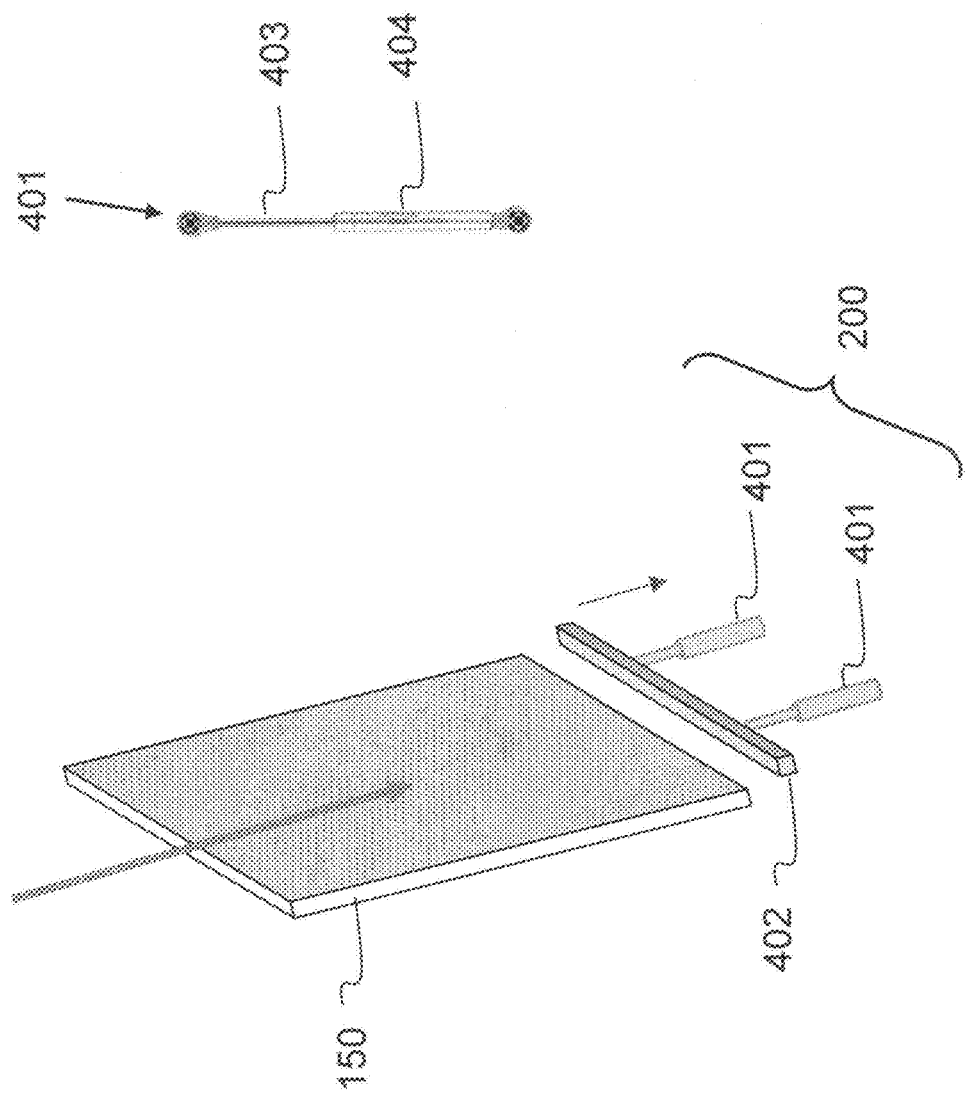
FIG. 4 is a diagram of a damping assembly for use in a radiographic detector storage slot.

FIG. 4 illustrates a damping assembly 200 including one or more pneumatic or hydraulic dampers 401, placed in a slot 130a, 130b, 130c, and connected to a receiving member, or suspension bar, 402 which makes contact with a leading edge of the detector 150 when the detector 150 is inserted into the slot 130a, 130b, 130c. The receiving member 402 may include a sufficiently linear and rigid member configured to contact a leading edge of the digital radiographic detector 150 as the detector 150 is manually inserted into the slot 130a, 130b, 130c. Because the receiving member 402 may include dimensions slightly smaller than a cross section of the storage slot 130*a*, 130*b*, 130*c*, it will contact the manually inserted digital detector 150 and prevent it from free falling, due to earth gravity, into the storage slot 130*a*, 130*b*, 130*c*. Thereby, the receiving member 402 contacts the detector 150 on the detector's bottom edge, or leading edge, and the dampers 401 slowly allow the receiving member 402 and the detector 150 to be controllably lowered into the slot 130*a*, 130*b*, 130*c*, by force of gravity on the detector 150. The damping assembly 200 may include only one pneumatic or hydraulic damper 401 per slot, or multiple dampers 401 may be used as illustrated in FIG. 4. The pneumatic or hydraulic dampers 401 may each include a shaft 403 that slides into or out of a tube 404 having a pneumatic or hydraulic mechanism therein to prevent free-wheeling insertion or extension of the shaft 403 therefrom.

The pneumatic or hydraulic dampers 401 of FIG. 4 allow the shaft 403 to slide into or out of the tube 404 at a controlled rate of speed due to pneumatic or hydraulic back pressure being gradually and continuously overcome by the weight of the detector 150, as is well known to a person having ordinary skill in the art. Similar to the rollers 301 described herein, the receiving member 402 may include a type of material with a preselected firmness to contact and cushion detectors 150 of various thicknesses when inserted into a slot, 130*a*, 130*b*, 130*c*. Such a material may include a type of elastomeric or foam rubber material with a preselected softness to contact the leading edge of the detector 150 when the detector is inserted into the slot 130*a*, 130*b*, 130*c*, without delivering a substantial impact force to the detector 150. Thus, the detector 150 is allowed to gently reach its resting position in the slot 130*a*, 130*b*, 130*c*, when the receiving member 402 and dampers 401 reach their lowest position therein. The selected material should include properties that are pathogen resistant and easily disinfected. When a detector 150 is manually removed from its lowest resting position within a storage slot 130*a*, 130*b*, 130*c*, the back pressure within dampers 401 are biased to slowly return the shafts 403 within dampers 401 and thereby the receiving member 402 to their initial receiving position at the upper terminus of their movement within the slot 130*a*, 130*b*, 130*c*.

In one embodiment, illustrated in FIG. 5, the damping assembly 200 may include a single hydraulic or pneumatic damper 401 connected to a receiving member 402 at an acute angle relative thereto, as compared to the perpendicular orientation of the receiving bar 402 and hydraulic or pneumatic dampers 401 of FIG. 4. The hydraulic or pneumatic damper 401 of FIG. 5 may be rotationally fixed at one end 501 to allow the hydraulic or pneumatic damper 401 to pivot as the damping assembly 200 moves between upper and lower terminal positions within the slot 130*a*, 130*b*, 130*c*. When a detector 150 is manually removed from its lowest resting position within a storage slot 130*a*, 130*b*, 130*c*, the back pressure within damper 401 is biased to slowly return the shaft 403 within damper 401 and thereby the receiving member 402 to their initial receiving position at the upper terminus of their movement within the slot 130*a*, 130*b*, 130*c*. The embodiments described herein may be retrofit into existing slots where detectors are stored.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A mobile radiography apparatus comprising:
    a moveable transport frame;
    an adjustable support structure coupled to the moveable transport frame;
    an x-ray source coupled to the adjustable support structure; and
    at least one detector storage slot configured to receive and to controllably lower at least one portable radiographic detector into the storage slot at a controlled speed.

2. The apparatus of claim 1, wherein the detector storage slot comprises a damping apparatus configured to act against earth gravity to controllably lower the at least one portable digital radiographic detector into the storage slot.

3. The apparatus of claim 2, wherein the damping apparatus comprises rollers configured to engage the portable digital radiographic detector, the rollers having a damped rotational velocity.

4. The apparatus of claim 3, wherein the damping apparatus comprises rollers configured to frictionally engage the portable digital radiographic detector on opposite sides thereof.

5. The apparatus of claim 2, wherein the damping apparatus is biased to return to an original position when the portable digital radiographic detector is removed from the storage slot.

6. The apparatus of claim 2, wherein the damping apparatus comprises a pneumatically or hydraulically controlled shaft attached to a suspension bar that contacts the portable digital radiographic detector.

7. A storage slot for a radiographic detector, the storage slot comprising:
    a receiving mechanism configured to contact the radiographic detector when the radiographic detector is inserted into the storage slot; and
    a damping apparatus connected to the receiving mechanism to prevent the receiving mechanism and the radiographic detector from free falling into the storage slot.

8. The storage slot of claim 7, wherein the damping apparatus is configured to act against earth gravity to controllably lower the digital detector into the storage slot.

9. The storage slot of claim 8, wherein the damping apparatus comprises rollers having a damped rotational velocity.

10. The storage slot of claim 7, wherein the damping apparatus comprises a pneumatically or hydraulically controlled shaft.

11. The apparatus of claim 9, wherein the rollers are configured to frictionally engage the portable digital radiographic detector on opposite sides thereof.

12. The apparatus of claim 7, wherein the damping apparatus is biased to return to an original position when the portable digital radiographic detector is removed from the storage slot.

13. The apparatus of claim 7, wherein the damping apparatus comprises a pneumatically or hydraulically controlled shaft attached to a suspension bar that contacts the radiographic detector.

14. The apparatus of claim 13, wherein the pneumatically or hydraulically controlled shaft is attached to the suspension bar at an angle less than sixty degrees.

15. A mobile radiography apparatus comprising:
a height adjustable x-ray source attached to a moveable transport frame; and
at least one detector storage slot configured to receive and to controllably lower at least one portable radiographic detector into the storage slot at a controlled speed.

16. The apparatus of claim 15, wherein the detector storage slot comprises a damping apparatus configured to act against earth gravity to controllably lower the at least one portable digital radiographic detector into the storage slot.

17. The apparatus of claim 16, wherein the damping apparatus comprises rollers configured to engage the portable digital radiographic detector, the rollers having a damped rotational velocity.

18. The apparatus of claim 17, wherein the damping apparatus comprises rollers configured to frictionally engage the portable digital radiographic detector on opposite sides thereof.

19. The apparatus of claim 17, wherein the damping apparatus is biased to return to an original position when the portable digital radiographic detector is removed from the storage slot.

20. The apparatus of claim 16, wherein the damping apparatus comprises a pneumatically or hydraulically controlled shaft attached to a suspension bar that contacts the portable digital radiographic detector.

* * * * *